United States Patent [19]

Bucalo

[11] 4,197,846
[45] Apr. 15, 1980

[54] METHOD FOR STRUCTURE FOR SITUATING IN A LIVING BODY AGENTS FOR TREATING THE BODY

[76] Inventor: Louis Bucalo, 155 Roberts St., Holbrook, N.Y. 11741

[21] Appl. No.: 590,268

[22] Filed: Jun. 25, 1975

Related U.S. Application Data

[62] Division of Ser. No. 513,295, Oct. 9, 1974, Pat. No. 4,005,699.

[51] Int. Cl.² ............................................. A61J 2/00
[52] U.S. Cl. ........................... 128/218 P; 128/213 R
[58] Field of Search ................ 128/1 R, 1.3, 1.5, 2 A, 128/156, 172, 213, 214 R, 218 P, 260, 264, 265, DIG. 8, DIG. 25; 3/36; 424/365

[56] References Cited

U.S. PATENT DOCUMENTS

| 793,099 | 6/1905 | Sapp | 128/218 P |
|---|---|---|---|
| 2,163,588 | 6/1939 | Cornish | 128/156 |
| 2,796,381 | 6/1957 | Borst | 424/365 |
| 2,939,673 | 6/1960 | Rosholt | 128/1.3 |
| 3,538,917 | 11/1970 | Selker | 128/DIG. 25 |
| 3,592,185 | 7/1971 | Frei et al. | 128/260 |
| 3,659,600 | 5/1972 | Merrill | 128/260 |
| 3,794,041 | 2/1974 | Frei et al. | 128/1.3 |
| 3,879,511 | 4/1975 | Goodhart et al. | 424/365 |

OTHER PUBLICATIONS

Kaiser et al., "IEEE Transactions on Magnetics", vol. MAG. 6, No. 3, Sep., 1970, pp. 694–698.
Newbower, "IEEE Transactions on Magnetics", vol. MAG. 9, No. 3, Sep., 1973, pp. 447–450.

Primary Examiner—William E. Kamm
Attorney, Agent, or Firm—Steinberg & Blake

[57] ABSTRACT

By way of a suitable syringe, for example, there is injected into the tissue of a living being an absorbable viscous substance in which a plurality of solid bodies are suspended to an extent sufficient to be distributed throughout the viscous substance and in an amount sufficient to change the characteristics of the tissue receiving the injection. The absorbable viscous substance with the solid bodies suspended therein may be initially enclosed in a plunger assembly capable of being connected with an injection needle.

17 Claims, 3 Drawing Figures

METHOD FOR STRUCTURE FOR SITUATING IN A LIVING BODY AGENTS FOR TREATING THE BODY

CROSS REFERENCE TO RELATED APPLICATION

This application is a division of application Ser. No. 513,295, filed Oct. 9, 1974 now U.S. Pat. No. 4,005,699.

BACKGROUND OF THE INVENTION

The present invention relates to methods, materials, and devices to be used in providing for living beings treatments such as enlarging tissue, alleviating incontinence, and medicating with suitable drugs or the like.

As is well known, many individuals are troubled by the fact that parts of their bodies are not sufficiently attractive, symmetrical or physically functional. For example, patients are often disturbed by the feature damage resulting from accidents while male individuals are in many cases disturbed by the fact that the penis is too small. Also, in some cases individuals suffer from incontinence because of an incapability of controlling the urethra or anal canal.

Also, in connection with medication it is often required to repeatedly inject into the tissue of an individual a suitable medication such as drugs or the like for the purpose of treating an individual. This requirement of repeated injections is of course highly undesirable, representing one of the major inconveniences involved in the treatment of many different types of ailments.

Many attempts have been made to solve problems of the above type. Thus, for example, it is known to introduce into the tissue quantities of a substance such as silicone, in order to enlarge tissue, but this solution to the problem of enlarging portions of body tissues is highly unsatisfactory since it results only in maintaining in the interior of the living being a quantity of a foreign substance which is uncontrollable in form and undesirable because of potential migration and difficulty in situating the substance at a desired location.

Procedures such as introducing a foreign substance into the body of a living being have been used in connection with relief of incontinence, but up to the present time no satisfactory solution has been provided for this problem, because of the difficulty of defining the configuration of the injected materials and the unstable nature of the implant form and shape.

SUMMARY OF THE INVENTION

It is accordingly a primary object of the present invention to provide methods, materials, and devices for avoiding the above drawbacks.

In particular, it is an object of the present invention to provide methods and materials suitable for enlarging body tissue.

Also it is an object of the present invention to provide a method and structure for alleviating incontinence without requiring any surgical procedures.

Furthermore, it is an object of the present invention to provide a method and structure according to which it becomes possible to provide an individual with medication such as suitable drugs or the like, without, however, requiring repeated injections of the medication while at the same time enabling the individual to be maintained under a desired influence of the medication over a considerable period of time during which with conventional procedures repeated injections would have been required.

According to the method of the invention a living being may be treated by injecting with a syringe into tissue of the living being an absorbable viscous substance in which a plurality of solid bodies are suspended to an extent sufficient to be distributed throughout the viscous substance and in an amount sufficient to change the characteristics of the tissue receiving the injection.

With the structure of the invention an absorbable viscous substance which has a plurality of solid bodies suspended therein is enclosed within a plunger assembly suitable for connection to an injection needle.

BRIEF DESCRIPTION OF DRAWINGS

The invention is illustrated by way of example in the accompanying drawings which form part of this application and in which.

DESCRIPTION OF PREFERRED EMBODIMENTS

Figure 1:
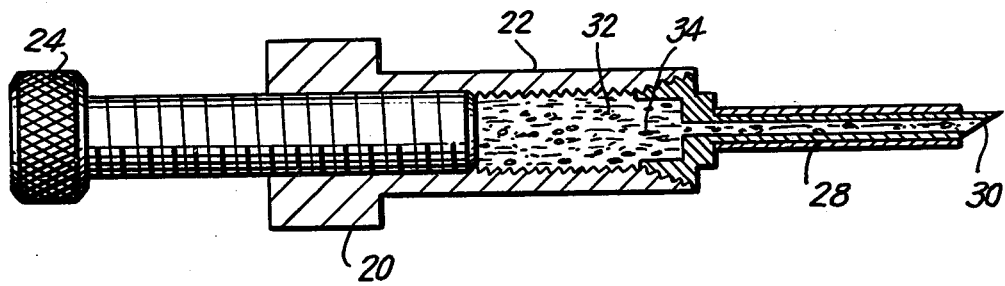
FIG. 1 is a fragmentary partly sectional schematic illustration of a syringe containing materials according to the invention which are introduced into tissue according to the method of the invention.

In connection with the enlargement of parts of the body in a living being, the method of the invention involves introducing into the tissue which is to be enlarged a viscous substance in which bodies are suspended while being distributed throughout the substance. The introduction of the substance with the bodies suspended therein is carried out, for example, by way of a screw type syringe 20 as schematically shown in FIG. 1. Thus, the syringe 20 has a hollow barrel 22 which receives the screw plunger 24. The outlet of the barrel 22 is connected to the needle 28 the tip 30 of which is introduced into the tissue at the part thereof which is to receive the materials (32 and 34) of the invention. These materials are shown in the barrel 22 in FIG. 1. Thus FIG. 1 shows a viscous substance 32 having the bodies 34 suspended therein and distributed therethrough.

In the preferred embodiment of the invention, the substance 32 is to be absorbed by the body and it may take the form of a vegetable oil or gelatin. The bodies 34 are preferably particles, but may include some elongated fibers as illustrated schematically in FIG. 1. Sufficient bodies 34 are suspended in the substance 32 so as to be distributed completely therethrough with the bodies 34 randomly engaging each other. The bodies 34 are made of materials which will be compatible with the body. Thus they may take the form of particles or fibers of gold, platinum, magnetic materials such as a platinum-cobalt alloy, gold plated magnetic materials, or the like, and it is also possible to use suitable absorbable materials or plastic materials for the bodies 34 combined with x-ray opaque materials.

According to a particular feature of the invention it is preferred to use for the substance 32 viscous hydrogenated vegetable oil, because in this case the time of absorption of the viscous substance may be controlled by the degree of hydrogenation, so that after the viscous substance 32 has been absorbed and replaced by tissue there remains in the living being an enlarged tissue portion composed of natural body tissue which itself has grown into the spaces between the bodies 34. Such methods and materials may effectively be used for cosmetic purposes such as changing facial features, or the like.

The use of varying degrees of hydrogenated cottonseed oil may be used for temporary implantation of solids. Thus, the viscous substance 32 may be very fluid unhydrogenated cottonseed oil which will be absorbed in a matter of days and the particles or fibers 34 composed of fully hydrogenated cottonseed oil which has the hardness of bone and which will require months for absorption. In this way varying rates of absorption and replacement by tissue are possible by varying the percentages of differentially hydrogenated components, as well as their size and shape. Such a method provides a temporary but effective result which may be repeated and is self-eliminating.

In addition, the varying rates of absorption may be utilized for the application of controllably releasing drugs and medications, such drugs and medications being absorbed at a rate controlled by the degree of hydrogenation of the injected vegetable oil, particles, as well as the size distributions of the absorbable particles rather than by chemical composition.

Thus, the particles, such as solid particles of hydrogenated vegetable oil may be impregnated with a suitable drug, medication or the like to be released over a considerable period of time in a controlled manner into the body. In addition, however, it is to be noted that the drugs, medication, or the like to be released to the body can be impregnated into any particles compatible with and capable of being absorbed by the body. Thus, instead of a material such as hydrogenated vegetable oil, it is possible to use a material such as cat gut. Such cat gut can be divided up into relatively small particles which when placed in a suitable evacuated atmosphere can have impregnated into the pores thereof an agent such as a suitable antibiotic, drug, or the like. Thus, such cat gut particles when chopped up into a fine particulate form can be used in the same way as solid particles of hydrogenated vegetable oil which of course can also be impregnated with suitable medications, drugs, or the like as pointed out above. Therefore, with the present invention it is possible to utilize any solid particles which will be absorbed by the body and which before being introduced into the body are impregnated with the agent which is to be slowly released to the body at a desired rate.

In addition, such methods and materials may be used in the penis for enlarging the same. For some individuals with permanent damage to the erectile systems, it is feasible to permanently enlarge the penis so that it can at any time penetrate into the vagina for effectively carrying out sexual intercourse. Thus, for this latter purpose a substance 32 such as hydrogenated vegetable oil having bodies 34 suspended therein can be introduced directly into the penile shaft in a manner according to which the substance is distributed along the penile shaft. This can be done by initially introducing the needle 30, and withdrawing the needle while simultaneously displacing the plunger 24 further into the barrel 22 so as to distribute the substance 32 and the bodies 34 therein in a desired manner along the penile shaft.

With the introduction of such materials into the penis, it may be permanently enlarged to an extent sufficient for reliably achieving penetration of the vagina whenever desired, and then as a further increase in the size of the penis takes place by natural means or artificial stimulation, the tissue itself will become further elongated because the injected implant will not damage the normal physiology as does surgically applied implants.

Figure 2:
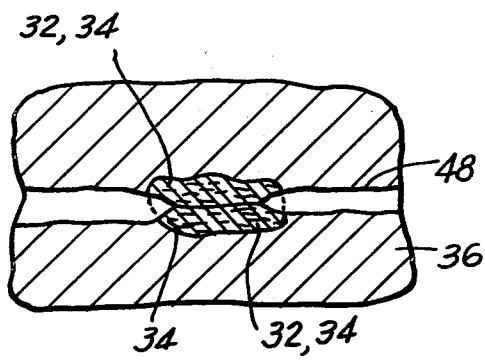
FIG. 2 is a schematic illustration of materials situated in tissue for the purpose of constricting a region of a body cavity.

Furthermore, as is well known, certain individuals suffer from incontinence in that they are unable to control discharges through the urethra or anal canal. For such individuals it is possible to introduce a ring of the substance 32 with the bodies 34 suspended therein around the passage 48 in the tissue 36 so as to relieve the condition of incontinence as shown in FIG. 2. In this case, the annular deposition of the substance 32 and the bodies 34 suspended therein around the urethra or anal canal is carried out in such a way that these tubular body passages are constricted somewhat by the introduced substance 32 and the bodies 34 suspended therein, in order to close the body passage 48 to prevent discharge therethrough except when normal urination or defecation pressure is provided to an extent sufficient to open the passage in opposition to the force of the deposited substance 32 and the bodies 34 suspended therein. Of course, in this case also, in connection with the alleviation of incontinence, it is preferred to use an absorbable substance 32 which will become replaced by living tissue which grows into the spaces between the fibers 34. Furthermore, it is preferred to use fibers which are opaque to x-ray such as fibers of gold, since such materials are most compatible and may be located by x-ray to verify their proper location. Also for these purposes (alleviation of incontinence, e.g.) injection of a mass of springy fibers is highly desirable.

Figure 3:
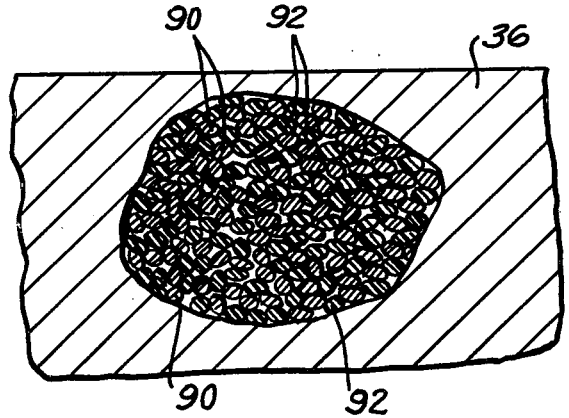
FIG. 3 is a schematic illustration of a further embodiment of materials situated in tissue in accordance with the invention.

A further embodiment of the invention illustrated in FIG. 3 involves injecting into the tissue 36 both magnetic particles 90 and elastic particles 92 made of any suitable plastic material which is compatible with the body such as, for example, Dacron which can be placed in the form of small elastic particles. All of these particles are initially in a solution with which they are injected, this solution being absorbed by the body so as to provide the tissue with the mass of magnetic particles 90 and the elastic particles 92 intermingled therewith as illustrated in FIG. 3. With this arrangement it is possible to regulate the extent to which the elastic particles are compressed by controlling the extent to which the magnetic particles are magnetized. Thus if the magnetic particles 90 are magnetized to a large extent, so that they attract each other with a considerable force, the elastic particles will be compressed to a relatively great extent, while if the magnetic particles are not magnetized with a particularly large magnetic force, the elastic particles will have a more relaxed condition. The advantage of this arrangement is that it is possible to inject with a conventional syringe, for example, directly into the mass of particles 90, 92 any drug or other medication which is intended to seep at a predetermined rate into the body. After such a drug or other medication is injected into the mass of particles 90, 92, it is possible to determine how the individual is reacting to the drug or other medication. If it is indicated that these materials are being released too rapidly, then the extent of magnification of the particles 90 is reduced so that the squeezing force on the medication, distributing the latter to the body, will be reduced and thus the rate of seepage into the body will be diminished. On the other hand, if it is felt that the medication is not being released quickly enough so that, in effect, the dosage should be increased, then the extent of magnification of the particles 90 is increased to compress the elastic bodies to a greater extent and thus cause the medication to be delivered to the body at a greater rate, or in other words in a lesser period of time. Of course with such an arrangement when the medication is entirely consumed it is possible again to inject a further amount of medication into the mass of particles 90,92. Thus with this arrangement it is possible to achieve in an extremely effective manner a controlled release of medication into the body. The extent of magnetization of the particles 90 can be regulated in accordance with the strength of the magnetic field which is provided at the exterior of the body to have its lines of flux influence the particles 90, and of course the magnetization can be reduced by utilizing an alternating field as is well known.

What is claimed is:

1. In a method of treating a living being, the step of injecting with a syringe, into tissue of the living being, an absorbable liquid substance, in which a plurality of solid bodies of hydrogenated vegetable oil are suspended to an extent sufficient to be distributed throughout the liquid substance, in an amount sufficient to change the characteristics of the tissue receiving the injection, said solid bodies having the property of being absorbable at a slower rate than the liquid substance.

2. In a method as recited in claim 1 and wherein the solid bodies composed of hydrogenated vegetable oil are impregnated with a drug which will be released during absorption of the solid bodies by the body.

3. In a method as recited in claim 2 and wherein said liquid substance also has a drug combined therewith for release to the body.

4. In a method as recited in claim 1 and wherein the liquid substance is hydrogenated vegetable oil.

5. In a method of treating a living being, the step of injecting with a syringe, into tissue of the living being, an absorbable liquid substance, in which a plurality of solid bodies are suspended to an extent sufficient to be distributed throughout the liquid substance, in an amount sufficient to change the characteristics of the tissue receiving the injection, at least a portion of the bodies being non-absorbable and in the form of a springy mass of elongated fibers, said injecting step including distributing the liquid substance with the bodies suspended therein in tissue around a tubular passage through which discharge is required from time to time with the liquid substance and bodies therein at least partially constricting the tubular passage for alleviating incontinence.

6. In a method as recited in claim 5 and wherein at least a portion of the non-absorbable bodies are opaque to x-rays.

7. In a method of treating a living being, the steps of injecting with a syringe, into tissue of the living being, an absorbable liquid substance, in which a plurality of solid bodies are suspended to an extent sufficient to be distributed throughout the liquid substance, in an amount sufficient to change the characteristics of the tissue receiving the injection, said solid bodies including non-absorbable magnetizable bodies and elastic bodies intermingled with the magnetizable bodies to be compressed thereby to a predetermined extent in accordance with the degree to which the magnetizable bodies are rendered magnetic and attract each other, and injecting into a mass in the tissue, made up of the magnetizable and elastic bodies, a medication to be released into the body at a predetermined rate in accordance with the extent to which the magnetizable bodies attract each other, so as to control the rate of release of the medication situated in the tissue at the bodies.

8. In a method as recited in claim 7 and including the step of magnetizing said magnetizable bodies to an extent which will determine the rate of release of medication into the body.

9. For use in the treatment of a living being, an absorbable liquid substance having suspended therein a plurality of solid bodies composed of hydrogenated vegetable oil and having the property of being absorbed at a slower rate than the liquid substance, and a plunger assembly, suitable for connection to an injection needle, enclosing said liquid substance and said solid bodies.

10. The combination of claim 9 and wherein said liquid substance contains a drug to be absorbed by the body and said solid bodies are impregnated with a drug to be absorbed by the body with the solid bodies.

11. The combination of claim 9 and including an injection needle, and wherein a screw type fitting joins said injection needle to said plunger assembly.

12. The combination of claim 9 and wherein said solid bodies are impregnated with a drug which will be released during absorption of the solid bodies.

13. The combination of claim 9 and wherein said liquid substance has a drug combined therewith for release to the body.

14. The combination of claim 9 and wherein the liquid substance is hydrogenated vegetable oil.

15. For use in the treatment of a living being, an absorbable liquid substance having suspended therein a plurality of solid bodies at least a portion of which are non-absorbable and in the form of a springy mass of elongated fibers, and a plunger assembly, suitable for connection to an injection needle, enclosing said liquid substance and said solid bodies.

16. The combination of claim 15 and wherein at least a portion of the solid bodies are opaque to x-rays.

17. For use in the treatment of a living being, an absorbable liquid substance having suspended therein a plurality of solid bodies, said solid bodies including magnetizable bodies and elastic bodies intermingled with said magnetizable bodies, and a plunger assembly, suitable for connection to an injection needle, enclosing said liquid substance and said solid bodies.

* * * * *